United States Patent [19]

Scherowsky et al.

[11] Patent Number: 4,966,726
[45] Date of Patent: Oct. 30, 1990

[54] CHIRAL REACTION PRODUCTS PRODUCED FROM MESOGENIC MOLECULAR STRUCTURAL ELEMENTS AND BIFUNCTIONALLY REACTIVE TARTARIC ACID DERIVATIVES, AND THEIR USE AS DOPANTS IN LIQUID CRYSTAL PHASES

[75] Inventors: Günter Scherowsky; Manel Gunaratne, both of Berlin, Fed. Rep. of Germany

[73] Assignee: Hoechst Aktiengesellschaft, Frankfurt am Main, Fed. Rep. of Germany

[21] Appl. No.: 222,340

[22] Filed: Jul. 18, 1988

Related U.S. Application Data

[63] Continuation of Ser. No. 14,290, Feb. 13, 1987, abandoned.

[30] Foreign Application Priority Data

Feb. 17, 1986 [DE] Fed. Rep. of Germany ....... 3604898

[51] Int. Cl.$^5$ ............... C09K 19/10; C09K 19/30; C07D 317/26; G02F 1/13
[52] U.S. Cl. ............... 252/299.6; 549/450; 549/451; 558/389; 558/398; 558/399; 558/411; 558/414; 558/416; 558/419; 558/420; 558/423; 558/426; 558/430; 558/431; 558/454; 560/1; 560/55; 560/59; 560/65; 560/110; 560/112; 560/116; 560/118; 560/125; 560/126; 560/180; 562/887; 564/152; 564/155; 252/299.61; 252/299.63; 252/299.66; 350/350 R; 350/350 S
[58] Field of Search ........... 549/369, 371, 372, 20, 549/21, 22, 450, 449, 451, 452, 453, 454; 544/295, 296, 298, 315, 322, 330, 357, 336; 558/399, 430, 416, 419, 414, 454, 420, 423, 426, 431, 389, 398, 411, 431; 560/1, 118, 116, 117, 125, 126, 180, 55, 112, 110, 59, 65; 252/299.63, 299.66, 299.01, 299.6, 299.61; 350/350 R, 350 S; 564/182, 188, 201, 152, 155; 562/887

[56] References Cited

U.S. PATENT DOCUMENTS

| | | | |
|---|---|---|---|
| 4,264,148 | 4/1981 | Göbl-Wunsch et al. | 252/299 X |
| 4,584,120 | 4/1986 | Fujii et al. | 560/118 X |
| 4,650,600 | 3/1987 | Heppke et al. | 252/299.01 |
| 4,673,529 | 6/1987 | Sugimori et al. | 560/118 X |
| 4,686,289 | 8/1987 | Huynh-Ba et al. | 558/409 X |

FOREIGN PATENT DOCUMENTS 0168043 1/1986 European Pat. Off. . .

Primary Examiner—John W. Rollins
Assistant Examiner—W. Catchpole
Attorney, Agent, or Firm—Curtis, Morris & Safford

[57] ABSTRACT

The new compounds produced from a molecular structural element with two chirality centers and at least one mesogenic structural element are defined by the general formula (I)

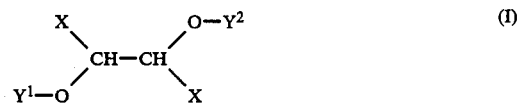

in which the symbols have the following meaning:
$Y^1 =$ H, $(C_1-C_{10})$alkyl, MC—$CH_2$ or MC—CO, MC denoting the molecular radical of a mesogenic carboxylic acid after splitting off a COOH group,
$Y^2 = (C_1-C_{10})$alkyl, MC—$CH_2$ or MC—CO, it being possible for $Y^1$ and $Y^2$ to jointly represent a MC—CH group, which is then part of a dioxolane ring,
$X =$ COOR$^1$, CONH$_2$, CONR$^2$R$^3$ or C≡N,
$R^1 = (C_1-C_{10})$alkyl or MC—CH$_2$, and
$R^2$, $R^3 =$ H and $(C_1-C_4)$alkyl or, independently of each other, $(C_1-C_4)$alkyl.

Said esters preferably find application as dopants in twistable liquid crystal phases in which they produce temperature compensation and twisting.

3 Claims, 2 Drawing Sheets

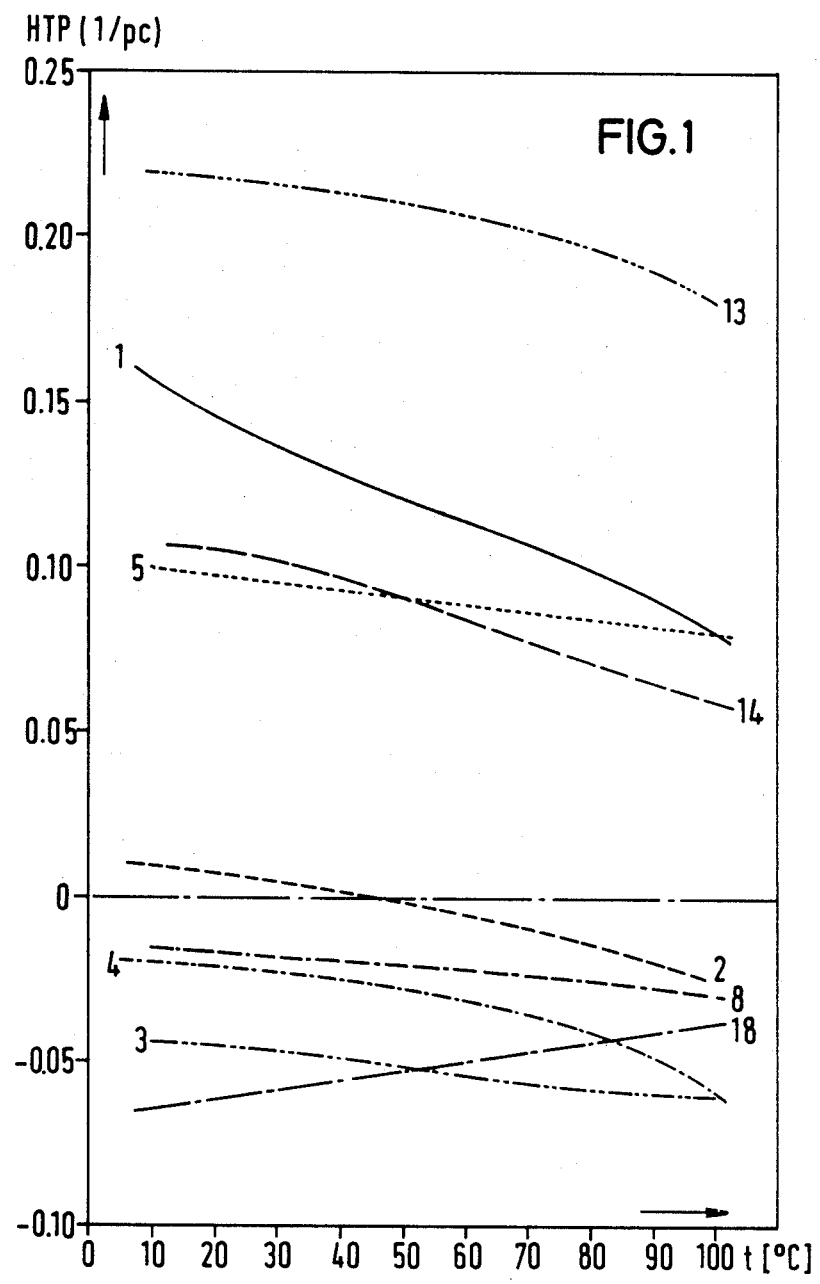

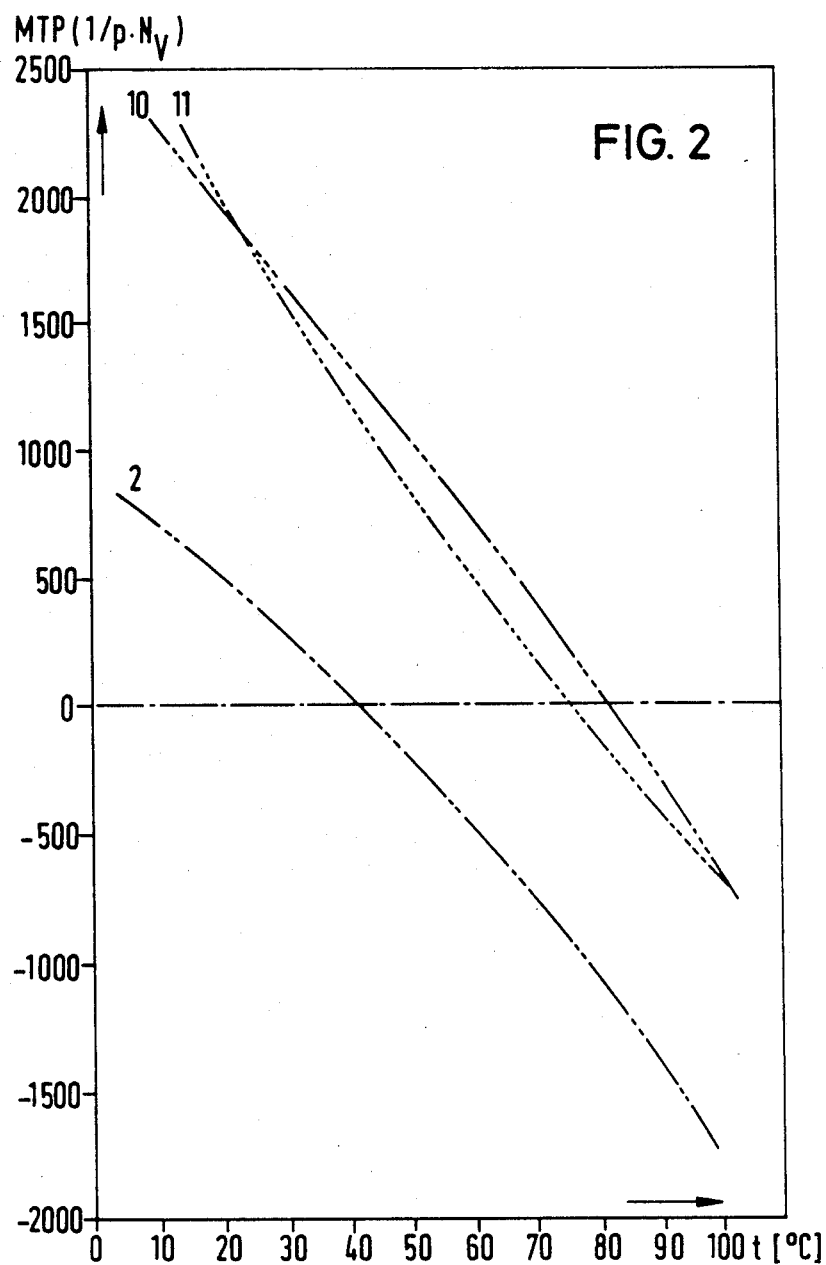

CHIRAL REACTION PRODUCTS PRODUCED FROM MESOGENIC MOLECULAR STRUCTURAL ELEMENTS AND BIFUNCTIONALLY REACTIVE TARTARIC ACID DERIVATIVES, AND THEIR USE AS DOPANTS IN LIQUID CRYSTAL PHASES

This application is a continuation of application Ser. No. 07/014,290, filed Feb. 13, 1987 now abandoned.

In general the characteristic curves of the electroptical effects used in liquid crystal displays vary with temperature. In particular, for a drive system employing multiplex operation, this results in difficulties which may lead to an undesirable restriction of the working temperature range. In the case of various electrooptical effects, the temperature dependence of the electrooptical characteristic curve can be advantageously influenced by addition of chiral compounds to the nematic liquid crystal via the temperature function of the pitch of the cholesteric helical structure thereby induced, as in the case of the cholesteric/nematic phase change effect, of the TN ("twisted nematic") cell and of the recently revealed SBE ("supertwisted brefringence effect"). The usual known dopants in general induce a pitch which increases with increasing temperature; dopants have also even been described recently which do not exhibit this often undesirable effect.

The addition of two different chiral dopants to nematic carrier substances is known from DE-C-2,827,471 (=U.S. Pat. No. 4,264,148); in this case one chiral dopant produces a right-handed twist in the nematic carrier substance, while the other produces a left-handed twist. A decrease in the pitch is achieved by means of such a doping but to achieve this effect relatively high total concentrations are necessary which may have a negative effect on the other material parameters.

DE-A-3,333,677 describes, inter alia, reaction products (esters) of chiral butane-2,3-diol with mesogenic carboxylic acids which may simplify the optimization of the temperature compensation in liquid crystal phases even as an individual addition. Said known esters often have twisting powers, however, which are still too low for certain applications.

The object of the present invention is therefore to discover new compounds which produce an optimization of the temperature compensation and also a considerable twisting of the liquid crystal phase even for relatively low added quantities when they are used, individually or as mixtures, as chiral dopants in liquid crystal phases; in addition, it should also be possible, starting from a comparable basic structure, to alter the properties of the molecule in a certain direction by fairly small molecular variations.

The starting point of the invention is the known compounds comprising a molecular structural element with two chirality centers and at least one mesogenic structural element. The new compounds are defined by the general formula (I)

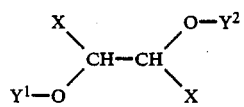

in which the symbols have the following meaning:

$Y^1$=H, $(C_1-C_{10})$alkyl, MC—$CH_2$ or MC—CO, MC denoting the molecular radical of a mesogenic carboxylic acid after splitting off a COOH group, $Y^2$=$(C_1-C_{10})$alkyl, MC—$CH_2$ or MC—CO, it being possible for $Y^1$ and $Y^2$ to jointly denote also a MC—CH group which is then part of a dioxolane ring, X=$COOR^1$, $CONH_2$, $CONR^2R^3$ or CEN, $R^1$=$(C_1-C_{10})$alkyl or MC—$CH_2$, $R^2R^3$=H and $(C_1-C_4)$alkyl or, independently of each other $(C_1-C_4)$alkyl.

The said compounds are tartaric acid diesters, or optionally substituted tartaric acid diamides or tartaric acid dinitriles, which are either singly or doubly esterified or etherified at the OH groups.

A further achievement of the object set is a twistable liquid crystal phase containing at least one chiral compound, wherein the phase contains at least one compound of the general formula (I) as a chiral compound. The term "twistable liquid crystal phase" is to be understood to mean nematic, cholesteric, tilted smectic, in particular smectic C ($S_c$ or SmC), phases.

The novel twistable liquid crystal phases consist of 2 to 20, preferably 2 to 15 components, including at least one of the chiral dopants claimed according to the invention. The other constituents are preferably selected from the known compounds having nematic, cholesteric and/or tilted smectic phases, which include, for example, Schiff's bases, biphenyls, terphenyls, phenylcyclohexanes, cyclohexyl biphenyls, pyrimidines, cinnamic acid esters, cholesterol esters, and variously bridged, terminally polar polynuclear esters of p-alkylbenzoic acids. In general, the liquid crystal phases obtainable commercially already exist, before the addition of the chiral dopant, as mixtures of a wide variety of components, at least one of which is mesogenic i.e. a compound which, in the form of a derivative or mixed with certain associated components, exhibits a liquid crystal phase [=permits at least one enantiotropic (clearing point>melting point) or monotropic (clearing point<melting point) mesophase formation to be expected].

Using the newly developed compounds as dopant, it is possible to achieve a high twisting with a small quantity of dopant in liquid crystal phases, it being possible, in addition, for the compounds, individually or as a mixture, to have a pitch which is substantially independent of temperature change, i.e. the increase or decrease in the pitch is, in general, in the range from 1% to 1 o/oo per K. The special properties of the novel compounds include, in addition, the fact that the sign of the temperature dependence of the twisting power ($d\beta/dT$) is independent of the sign of the pitch of the induced helical structure. By suitably varying the mesogenic radicals it is possible to induce either a right-handed or left-handed helix or even to achieve a helix inversion at a certain temperature, i.e. it is characteristic of these compounds that the handedness of twisting changes at a certain inversion temperature, said inversion temperature being in the present case between the solidification point and the clearing point of the particular liquid crystal phase; if commercially available liquid crystal phases are used, this means a temperature range from in particular −40° C. to +200° C., preferably −20° C. to +140° C. The novel compounds may further be used in thermotopography or for producing "blue phases" (=cholesteric systems with a relatively low pitch of e.g. less than 800 nm).

If the starting point in the synthesis of the said tartaric acid derivatives is the S,S-form instead of the R,R-form, curve shapes of the temperature dependence of the twisting power are observed which are mirrored at the temperature axis, i.e. the sign of the direction of rotation of the helix is interchanged. If the mesogenic acyl radicals in the molecule are converted into benzyl radicals

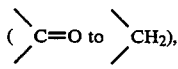

an increase in the HTP or MTP occurs, these and other terms used above and below being defined as follows:

HTP ("helical twisting power"): $1/p.c$, (p=pitch of the induced helix in $\mu m$, c=concentration of the chiral dopant in % by weight), MTP ("molecular twisting power"): $\beta = 1/p.N_v$ (p=pitch in m, $N_v$=concentration of the chiral dopant in mol/m$^3$). If the ester groupings are also converted into nitrile groups, the sign of the direction of rotation of the helix changes. In addition, the dinitrile exhibits a very good spontaneous polarization $P_s$ of 40 nC.cm$^{-2}$ (extrapolated to the pure compound), i.e. it is a suitable addition for the conversion of SmC phases into ferroelectric liquid crystal phases, said Ps being the better, the higher the values are in nC.cm$^{-2}$.

Of the compounds of the general formula (I) those are preferred in which the radical MC in MC—CH$_2$, MC—CO or MC—CH [expressed by the general formula (II)] has the following meaning:

$$R^4-(A^1-)_{n1}(B-)_{n2}(A^2-)_{n3} \qquad (II)$$

in which the symbols have the following meanings:

$R^4$=a straight-chain or branched (C$_1$-C$_{12}$)alkyl group, it being possible for one or two non-adjacent CH$_2$ groups to be replaced by O atoms, or if n1 =1, also F, Cl, Br or CN, $A^1$, $A^2$=independently of each other, 1,4-phenylene, diazine-2,5-diyl, diazine-3,6-diyl, 1,4-cyclohexylene, 1,3-dioxane-2,5-diyl, 1,3-dithiane-2,5-diyl or 1,4-bicyclo[2.2.2]octylene, it being possible for these groups to be at least singly substituted by F, Cl, Br, CN and/or (C$_1$-C$_{12}$)alkyl (one or two non-adjacent CH$_2$ groups are optionally replaced by O atoms), B=CO—O, O—CO, CH$_2$—CH$_2$, OCH$_2$, CH$_2$O, CH=N, N=CH, N=N, N(O)=N, and n1, n2, n3 =independently of each other, 0, 1 or 2, n1 and n3 not being 0 at the same time.

Of these compounds those are in turn preferred in which the symbols have the following meaning: $R^4$=straight-chain (C$_4$-C$_{10}$)alkyl it being possible for a CH$_2$ group to be replaced by an O atom, $A^1$, $A^2$=independently of each other, unsubstituted 1,4-phenylene, 1,4-cyclohexylene or diazine-2,5-diyl, B=CO—O or O—CO, n1=1, n2=0 or 1, and n3=1 or 2.

MC radicals are, however, also possible which are derived from chiral carboxylic acids such as substituted phenyl acetic acids, e.g. from 3,3,3-trifluoro-2-methoxy-2-phenylpropanoic acid.

In addition, in the general formula (I) the compounds are preferred in which the symbols have the following meaning: $Y^1=Y^2=$MC—CO or MC—CH$_2$ and X=COOR$^1$ with R$^1$=(C$_1$-C$_8$)alkyl, CONH$_2$ or C=N.

The liquid crystal phases contain in general 0.01 to 70 % by weight, in particular 0.05 to 50% by weight, of the novel dopant or dopants.

EXAMPLES

General working procedure for preparing compounds 1 to 12.

10 to 40 mg of dimethylaminopyridine and 1.5 mmol of the mesogenic carboxylic acid are added to 1 mmol of the tartaric acid derivative in 10 to 50 ml of anhydrous methylene chloride or dimethylformamide while stirring. At a temperature of 0° C., 1.5 mmol of dicyclohexylcarbodiimide are added and stirring is carried out for 10 minutes at this temperature and then for 20 h at room temperature. Precipitated urea is filtered off, the filtrate is evaporated down in vacuum and the residue left is taken up in methylene chloride. After any filtration necessary, the organic solvent is distilled off and the residue chromatographed on silica gel. The following compounds whose structures have been established by spectroscopic data and elementary analysis, are prepared by this procedure:

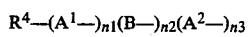

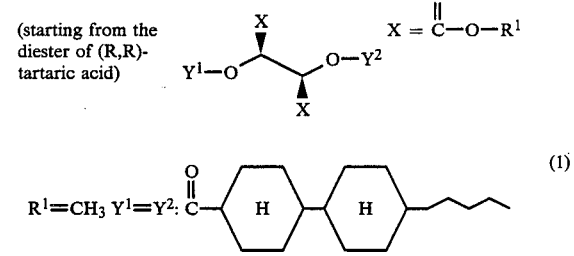

Dimethyl-(R,R)-(−)-2,3-bis(4'-trans-n-pentyl-4-trans-dicyclohexylcarbonyloxy)-1,4-butanedicarboxylate

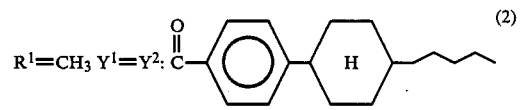

Dimethyl-(R,R)-(−)-2,3-bis[4-(trans-4-n-pentylcyclohexyl)-benzoyloxy]-1,4-butanedicarboxylate

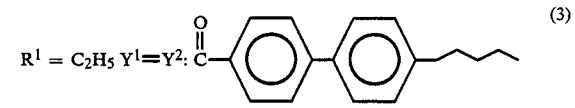

Diethyl-(R,R)-(−)-2,3-bis(4'-n-pentyl-4-diphenylcarbonyloxy)-1,4-butanedicarboxylate

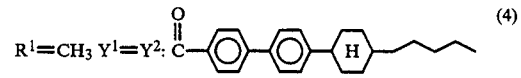

Dimethyl-(R,R)-2,3-bis-(4'-trans-n-pentylcyclohexyl-4-diphenylcarbonyloxy)-1,4-butanedicarboxylate

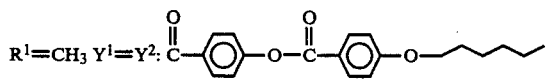
(5)

Dimethyl-(R,R)-(−)-2,3-bis[4-(4-n-hexyloxy-benzoyloxy)benzoyloxy]-1,4-butanedicarboxylate

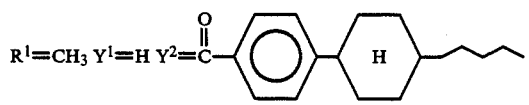
(6)

Dimethyl-(R,R)-(+)-2-[4-(trans-4-n-pentylcyclohexyl)-benzoyloxy]-3-hydroxy-1,4-butanedicarboxylate

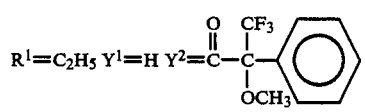
(7)

Diethyl-(R,R)-(+)-2-(3,3,3-trifluoro-2-methoxy-2-phenylpropanoyloxy)-3-hydroxy-1,4-butanedicarboxylate

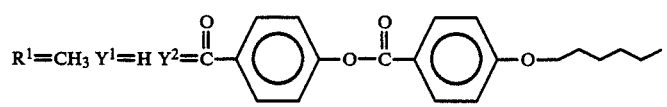
(8)

Dimethyl-(r,R)-(+)-2-[4-(4-n-hexyloxybenzoyloxy)-benzoyloxy]-3-hydroxy-1,4-butanedicarboxylate

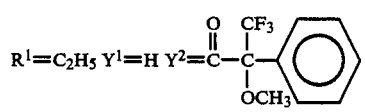
(9)

Diethyl-(R,R)-(+)-2-[4-(trans-4-n-pentylcyclohexyl]-benzoyloxy]-3-(3,3,3-trifluoro-2-methoxy-2-phenyl-propanoyloxy)-1,4-butanedicarboxylate

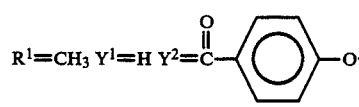
(10)

Diethyl-(R,R)-(−)-2,3-bis-[4-(trans-4-n-pentylcyclohexyl)benzoyloxy]-1,4-butanedicarboxylate

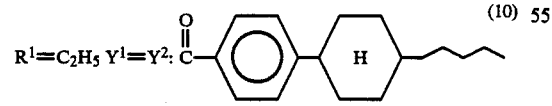
(11)

Di-n-octyl-(R,R)-2,3-bis-[4-(trans-4-n-pentylcyclohexyl)benzoloxy]-1,4-butanedicarboxylate (starting from the diester of (S, S)-tartaric acid)
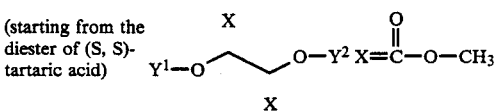
(12)

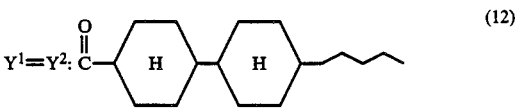

Dimethyl-(S,S)-2,3-bis-(4'-trans-n-pentyl-4-transdicyclohexylcarbonyloxy)-1,4-butanedicarboxylate Preparation of compound 13

To the solution of 10 mmol of diethyl-(R,R)-tartarate in 7 ml of acetonitrile, there are first added 20 mmol of thallium ethylate and then 27 mmol of 4-(trans-4-n-pentylcyclohexyl)-benzyl bromide so slowly that no heating occurs. The reaction mixture is then heated for 50 h at 58° C. and stirred for a further 14 h at room temperature. The thallium bromide precipitate produced is filtered off, the organic solvent is removed in vacuum and the residue left is chromatographed on silica gel.

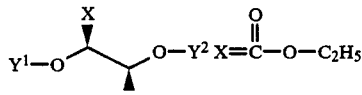
(13)

Diethy-(R,R)-2,3-bis-[4-(trans-4-n-pentylcyclohexyl)-benzyloxy]-1,4-butanedicarboxylate Preparation of compounds 14 and 15

The procedure is in accordance with the general working procedure given further above, but the starting compound is (R,R)-(+)-2,3-dimethoxy-1,4-butanoic diacid [see D. Seebach, Helv. Chim. Acta 60, 301 (1977)] and the corresponding alcohol.

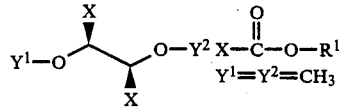

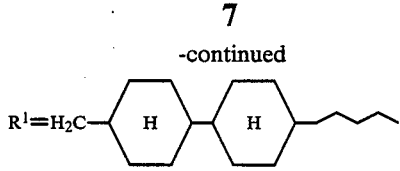

Di-(4-trans-n-pentyl-4-trans-dicyclohexylmethyl)-(R,R)-2,3-dimethoxy-1,4-butanedicarboxylate

Di-[4-(trans-4-n-pentylcyclohexyl)benzyl](R,R)-2,3-dimethoxy-1,4-butanedicarboxylate]

Preparation of compound 16

A mixture of 0.5 g (1.5 mmol) of 4-(trans-4-n-pentyl-cyclohexyl)-4-biphenylcarbaldehyde, 0.53 g of dimethyl-(R,R)-tartarate and 0.03 g of p-toluenesulphonic acid. $H_2O$ is stirred in 20 ml of cyclohexane at 0° C. and a molecular sieve (0.5 pm), finely powdered under cyclohexane, is added. The mixture is stirred for 2 h at 0° C. and stirred overnight at room temperature. Then 0.05 ml of trimethylamine are added. The suspension is filtered, the molecular sieve is washed with pentane and the combined organic phases are washed with 15% aqueous NaOH solution and then with $H_2O$. The organic phase is dried and evaporated down.

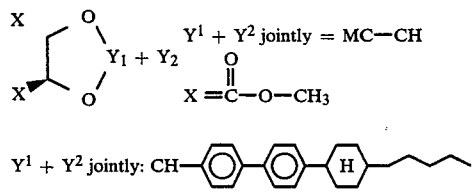

Dimethyl-(R,R)-2-[4(trans-4-n-pentylcyclohexyl)biphenyl]-1,3-dioxolane-4,5-dicarboxylate

Preparation of compound 17

About 3 ml of methanol saturated with $NH_3$ are added to a solution of 0.5 mmol of compound 13 in 2 ml of chloroform at −20° C. The solution is stirred for 3 days at room temperature. The precipitate produced is filtered off and recrystallized.

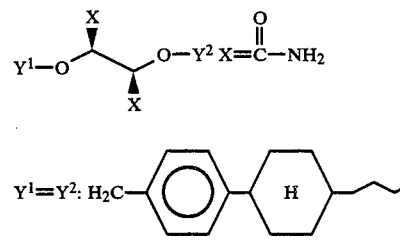

(R,R)-2,3-bis-[4-(trans-4-n-pentylcyclohexyl)benzyloxy]-1,4-butanedicarboxylic acid diamide

Preparation of compound 18

A solution of 0.3 mmol of compound 17 in 2 ml of pyridine is cooled to 0° C. and 0.6 mmol of $POLC_{13}$ are added dropwise, and stirring is then carried out for 1 h at 0° C. and 1 h at room temperature. After cooling again, 4 ml of $H_2O$ are added, and the precipitate deposited is then washed with water and taken up in ether. After distilling off the organic solvent, the residue is chromatographed on silica gel.

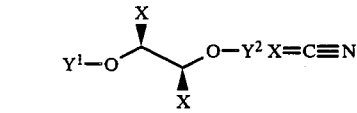

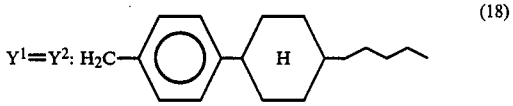

(R,R)-2,3-bis-[4-(trans-4-n-pentylcyclohexyl)benzyloxy]-1,4-butanedicarbonitrile

TABLE

| Compound No. | Temperature range (°C.) of the twisting power measurement | p.c (μm. % by weight) | Melting point (°C.) |
|---|---|---|---|
| 1 | 7–103 | 6 ← 13 | 97 |
| 2 | 3–98 | 101 → −40 | 74 |
| 3 | 10–100 | −22 → −16 | liquid |
| 4 | 4–100 | −51 → −16 | — |
| 5 | 10–100 | 10 → 13 | 105–106 |
| 6 | — | — | 45–50 |
| 7 | — | — | liquid |
| 8 | 10–100 | −29 → −16 | 90 |
| 9 | — | — | liquid |
| 10 | 10–100 | 31 → −99 | 48–50 |
| 11 | 10–100 | 39 → −136 | 38–40 |
| 12 | — | — | 99–101 |
| 13 | 10–100 | 4.5 → 5.7 | 70–73 |
| 14 | 10–100 | 9 → 18 | 120–122 |
| 15 | 10–100 | 6 → 14 | 74–76 |
| 16 | — | — | 110–112 |
| 17 | — | — | 212–213 |
| 18 | 10–100 | −16 → −25 | 154–156 |

The measurement of the twisting power is carried out in a commercially available nematic wide-range mixture ("RO-TN 404" manufactured by the Hoffmann-La Roche Aktiengesellschaft (Basel/Switzerland)) with a clearing point of 104° C. Insofar as measurable, the spontaneous polarization (Ps) is determined in the SmC phase of the commercially available compound "HEPTOAB" (manufactured, for example, by Frinton, USA) having the characteristic data "K 74.4 SmC 95.4 N 142.2 I".

In the accompanying drawing the HTP values (FIG. 1) are plotted as a function of the temperature for some of the novel compounds and the MTP values (FIG. 2) are also plotted for some compounds.

If one compares, for example, the shape of the curves of the HTP values of compounds 1 to 4 and 14 with each other in FIG. 1, either a left-handed or right-handed helix can be induced or a helix inversion takes place depending on the type of mesogenic radical. If the corresponding shape of the curve of compounds 5 and 8 is compared, it emerges that on changing over from the monoacyl derivative 8 to the diacyl derivative 5, the handedness of the induced helix changes, but the sign of the temperature dependence of the HTP does not. If the shape of the corresponding curve of the compounds 2, 13 and 18 is then compared, it emerges that the conversion of the acyl to a benzyl group leads to a sharper rise in the HTP, and the replacement of the ester group by nitrile groups again changes the handedness of the helix. FIG. 2 shows that although increasing the length of the alkyl radical in the ester functions from $CH_3$ to $C_2H_5$ leads to a considerable change in the inversion temperature with the same structure of the mesogenic radical, on increasing the length to $C_8H_{17}$ it then only changes slightly.

We claim:

1. A compound containing a molecular structural element with two chirality centers and at least one mesogenic molecular structural element, which compound is defined by the formula (I)

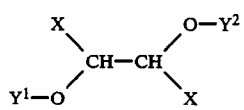
(I)

wherein:

$Y^1$ is H, $(C_1-C_{10})$alkyl, MC—$CH_2$ or MC—CO, MC being a mesogenic radical of the formula (II)

(II)

wherein:

$R^4$ is a straight-chain or branched $(C_1-C_{12})$alkyl group, in which one $CH_2$ group of the alkyl group can be replaced by an O atom, or if n1 is 1, $R^4$ also can be F, Cl, Br or CN, $A^1$, $A^2$ are, independently of each other, 1,4-phenylene or 1,4-cyclohexylene, B is CO—O or O—CO, n1, n2, n3 are, independently of each other, 0, 1 or 2, n1 and n3 not being 0 at the same time, and n1 and n3 not being 2 at the same time, $Y^2$ is $(C_1-C_{10})$alkyl, MC—$CH_2$ or MC—CO, or $Y^1$ and $Y^2$ together represent the group MC—CH, which is then part of a dioxolane ring, X is $COOR^1$, $CONH_2$, $CONR^2R^3$ or C≡N, $R^1$ is $(C_1-C_{10})$alkyl or MC—CH2 and one of $R^2$ and $R^3$ is H and the other is $(C_1-C_4)$alkyl or, independently of each other, both $R^2$ and $R^3$ are $(C_1-C_4)$alkyl.

2. A twistable liquid crystal phase containing 0.01 to 70% by weight of at least one of the chiral compounds of the formula (I) as claimed in claim 1.

3. A liquid crystal display element containing a liquid crystal phase as claimed in claim 2.

* * * * *